United States Patent [19]

Ikuno et al.

[11] 4,325,606
[45] Apr. 20, 1982

[54] CONNECTOR FOR A LIGHT GUIDE CABLE OF AN ENDOSCOPE

[75] Inventors: Yuji Ikuno, Hino; Kunio Kinoshita; Katsuyuki Kanehira, both of Hachioji, all of Japan

[73] Assignee: Olympus Optical Co., Ltd., Tokyo, Japan

[21] Appl. No.: 98,055

[22] Filed: Nov. 28, 1979

[30] Foreign Application Priority Data

Dec. 8, 1978 [JP] Japan .................. 53/151679

[51] Int. Cl.³ .............................................. G02B 7/26
[52] U.S. Cl. .................... 350/96.20; 350/96.26
[58] Field of Search ............. 350/96.10, 96.20, 96.23, 350/96.26; 339/182 L, 182 R, 182 S, 182 T, 183, 15, 16 R

[56] References Cited

U.S. PATENT DOCUMENTS

| 3,222,471 | 12/1965 | Steinkamp | 339/190 |
| 3,829,814 | 8/1974 | Straus | 339/183 |
| 3,880,148 | 4/1975 | Kanehira et al. | 350/96.26 |
| 4,181,397 | 1/1980 | Baker et al. | 350/96.20 |

*Primary Examiner*—John D. Lee

[57] ABSTRACT

A connector for a light guide cable of an endoscope comprises a connector body having one end connected to a light guide cable and the other end flush with a light-receiving face of a light guide inserted in the connected body, an electrically insulating member surrounding the connector body, and contacts embedded in the outer surface of the insulating member. None or almost none of its members protrude from the forward end or the outer periphery of the connector, whereby the connector may be fitted into a receptacle in fluid-tight fashion and can be easily cleaned and fully dried after cleaning.

25 Claims, 14 Drawing Figures

PRIOR ART

CONNECTOR FOR A LIGHT GUIDE CABLE OF AN ENDOSCOPE

This invention relates to an improvement of a connector for connecting a light guide cable of an endoscope to a light source console.

As shown in FIG. 1, an endoscope 1 is generally provided with a light guide cable 2 at its operation section. In the light guide cable 2 there are inserted an illumination optical fiber bundle, lead wires, a gas supply tube, a suction tube and other members. A connector 3 is attached to one end of the light guide cable 2 and can connect the cable 2 to a connector receptacle provided on a light source console.

As shown in FIG. 2 a plurality of connection pins 4, a tube 5 for an illumination optical fiber bundle and a gas supply tube fitting 6 are collected on and protrude from the free end of the known connector 3. The spaces between the pins 4, the tube 5 and the fitting 6 are so narrow that it is difficult to clean each of those members completely. For the same reason it is also difficult to quickly and fully dry these members after cleaning.

An object of this invention is to provide a connector for a light guide cable of an endoscope, in which members are inserted in fluid-tight fashion and from the connecting end of which none of the members protrudes, whereby the members can be completely and quickly cleaned and dried.

A connector according to this invention comprises a connector body having two ends, one end connected to a light guide cable of an endoscope and the other end flush with a light-receiving face of a light guide which is inserted in the connector body, an electrically insulating member surrounding the connector body and having an outer surface, and contacts embedded in the insulating member, having outer surfaces substantially flush with the outer surface of the insulating member and connected to lead wires which extend through the insulating member and the light guide.

This invention can be fully understood from the following detailed description with reference to the accompanying drawings in which.

Figure 1:
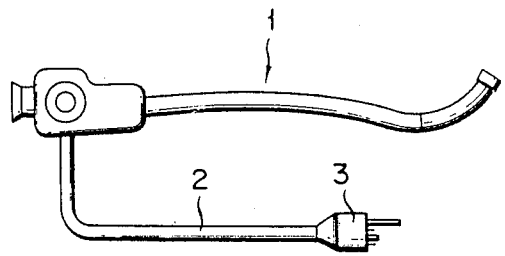
FIG. 1 shows an endoscope provided with a known connector.
Figure 2:
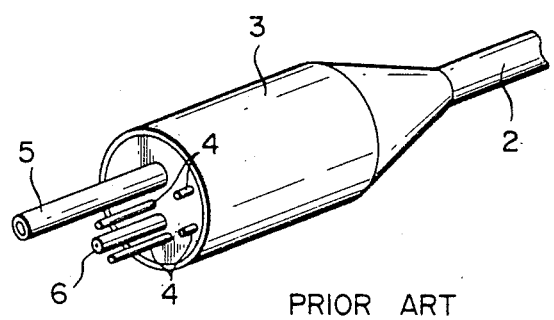
FIG. 2 is an enlarged perspective view of the connector of the endoscope shown in FIG. 1.
Figure 3:
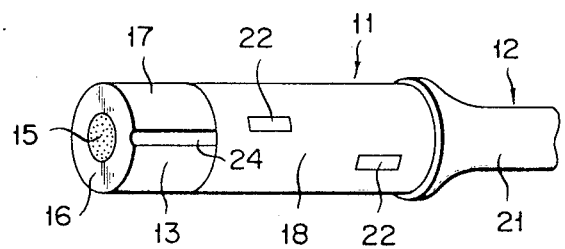
FIG. 3 is a perspective view of one embodiment of a connector according to this invention.
Figure 4:
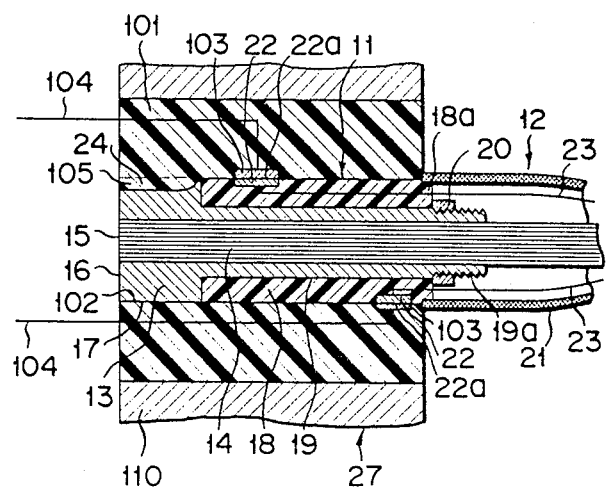
FIG. 4 is a longitudinal cross sectional view of the connector of FIG. 3 which is inserted in a receptacle of a light source console.

As shown in FIGS. 3 and 4, a connector 11 for a light guide cable of an endoscope comprises a connector body 13 and an electrically insulating member 18. The body 13 comprises a ring-shaped head 17 and a hollow cylindrical stem portion 19 integrally and coaxially formed with the head 17 and having a diameter smaller than that of the head 17. Both the head 17 and stem portion 19 are made of a non-corrosive metal such as stainless steel. The insulating member 18 surrounds the stem portion 19 of the body 13 and is made of, for example, polytetrafluoroethylene. The outer diameter of the insulating member 18 is equal to that of the head 17. Thus, the connector 11 is cylindrical as a whole. An external screw 19a is formed on the proximal end of the stem portion 19, and a nut 20 engages the screw 19a so as to fasten the insulating member 18 to the connector body 13.

One end of a light guide cable 12 is connected to the proximal end 18b of the insulating member 18. The other end of the cable 12 is connected to an operation section of an endoscope. The light guide cable 12 comprises a light guide 14, lead wires 23 and a flexible sheath 21 surrounding the light guide 14 and the lead wires 23. The guide 14 is an optical fiber bundle extending from the operation section of the endoscope. The lead wires 23 also extends from the operation section.

The light guide 14 extends through the connector body 13, and its light-receiving face 15 is substantially flush with the front end face 16 of the head 17. Strip contacts 22 made of electrically conductive material such as copper are embedded in the outer periphery 18a of the insulating member 18, spaced from each other in both the axial and circumferential directions of the insulating member 18. The outer surfaces 22a of the contacts 22 are substantially flush with the outer periphery 18a of the insulating member 18.

The lead wires 23 are led into the proximal end 18a of the insulating member 18 and extends axially in the member 18. The ends of the lead wires 23 in the member 18 are connected to the corresponding contacts 22. The other ends of the lead wires 23 are connected to an automatic exposure circuit and other electric circuits (both are not shown) which are provided in the operation section of the endoscope.

Formed in the outer periphery of the head 17 is a groove 24 which extends axially of the head 17 for setting the connector 11 in position with respect to a receptacle 27 provided in the front panel of a light source console 110.

The receptacle 27 of the light source 110 comprises a receptacle body 101 made of electrically insulating material such as polytetrafluoroethylene and strip contacts 103 made of electrically conductive material such as copper. The receptacle body 101 has a cylindrical hole 102 having a shape complementary to that of the connector 11. Contacts 103 are complementary to that of the connector 11. Contacts 103 are embedded in the inner periphery of the body 101 at such positions as to contact the corresponding contacts 22 of the connector 11 when the connector 11 is fully fitted in the hole 102. Lead wires 104 extend in the receptacle body 101 and each have one end connected to the corresponding contact 103 and the other end connected to a power source (not shown) disposed either in the console 110 or outside of the console 110. On the inner periphery of the hole 102 and at a position corresponding to the groove 24 of the connector 11, a protrusion 105 is provided, which has a shape complementary to that of the groove 24. When the protrusion 105 fits into the groove 24, the connector 11 is correctly positioned in the receptacle 27, whereby the contacts 22 come into contact with the contacts 103 and the light-receiving face 15 of the light guide 14 correctly faces the light source provided in the light source console 110.

As mentioned above, in the connector 11 of FIGS. 3 and 4 the contacts 22 are embedded in the insulating member 18 and do not protrude therefrom, and the light guide 14 does not protrude from the front end face 16 of the connector 11. The connector 11 is therefore cylindrical as a whole and can be easily and unfailingly fitted into the receptacle 27 in fluid-tightness. Further, except for the groove 24, it does not have convex or concave portions on its outer surface. This makes it easy to clean the connector 11 and to dry it quickly and completely after cleaning. Still further, since neither the light guide 14, contacts 22 nor lead wires 23 protrude from the outer surface or the front end face 16 of the connector 11, they would not be broken. So simply constructed, the connector 11 can be manufactured at a low cost.

Figure 5:
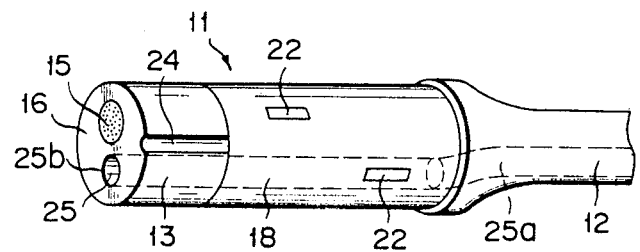
FIGS. 5 to 7 are perspective views of other embodiments of connectors according to this invention.

In another embodiment shown in FIG. 5, a fluid conducting passage 25 is formed in such a connector body 13 as shown in FIGS. 3 and 4. The passage 25 extends through the connector body 13 and communicates with a fluid channel (not shown) of an endoscope by means of a fluid conducting tube 25a extending through a light guide cable 12. To supply a liquid such as distilled water or liquid medicine into a body cavity through the passage 25, the end 25b of the passage 25 on the front end face 16 connected to a liquid source (not shown). To supply a gas such as air or carbon dioxide into a body cavity, the end 25b of the passage 25 is connected to a gas supply pump (not shown). To discharge a fluid from a body cavity, the end 25b of the passage 25 is connected to a suction pump (not shown). Instead of one fluid conducting passage, a necessary number of passages may be provided in the connector body 13 so that each of them supply a specific fluid into a body cavity or discharge it therefrom.

Figure 6:
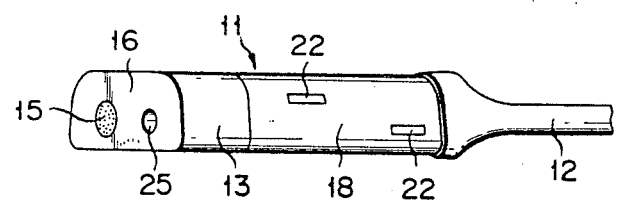

FIG. 6 shows another connector 11 according to this invention, which is identical with the connector 11 of FIG. 5 except that its section is semicircular. The receptacle into which the connector 11 is fitted has a hole having the same semicircular section, so that the contacts of the receptacle come into contact with the corresponding contacts of the connector 11 when the connector 11 is fully fitted in the hole.

Figure 7:
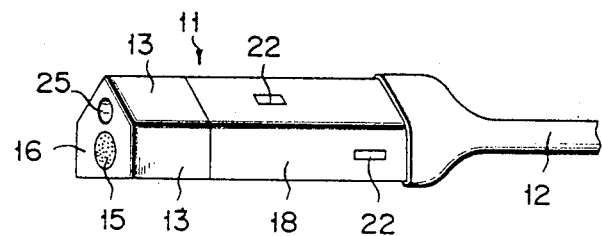

FIG. 7 shows still another connector 11 according to this invention, which is identical with the connector 11 of FIG. 5 except that its section is polygonal, for example pentagonal. The receptacle into which the connector 11 is fitted has a hold having a shape complementary to that of the connector 11, so that the same effect result in as in the connector of FIG. 6.

Unlike the connector of FIG. 5, the connectors 11 of FIGS. 6 and 7 need not be provided with a groove similar to the groove 24 of the connector of FIG. 5. Nor does the receptacle for receiving them need to have such a protrusion 105 as used in the receptacle shown in FIG. 5.

Figure 8:
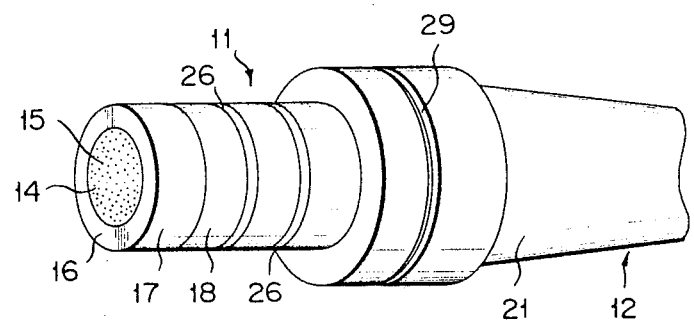
FIG. 8 is a perspective view of another embodiment of a connector according to this invention.
Figure 9:
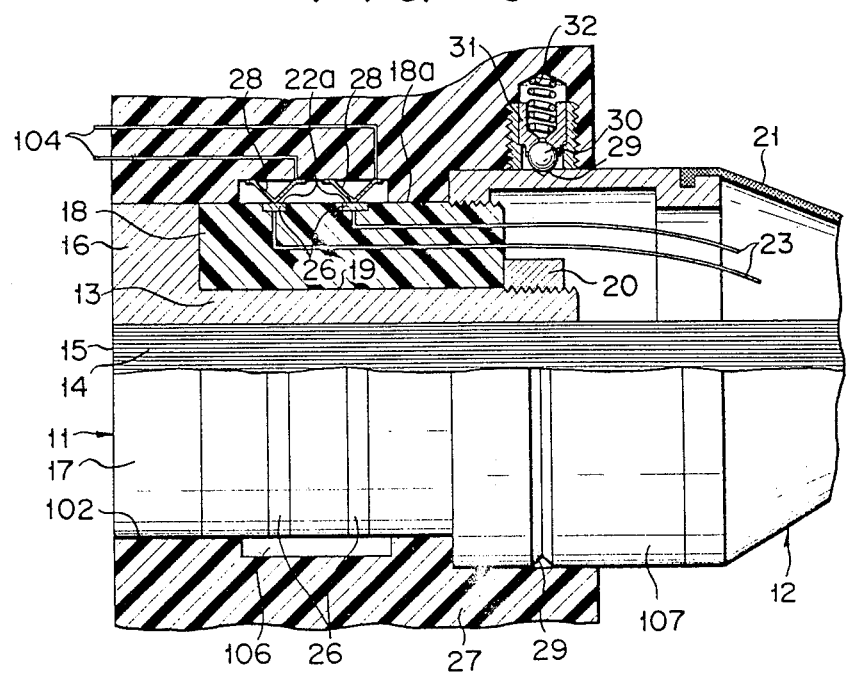
FIG. 9 is a longitudinal cross sectional view of the connector of FIG. 8 which is inserted in a receptacle of a light source console.

FIGS. 8 and 9 show another connector 11 according to this invention. This connector 11 differs from the connector of FIG. 5 in the following respects. First, ring-shaped contacts 26 are embedded in the outer periphery 18a of a hollow cylindrical insulating member 18. Secondly, an annular groove 106 is formed in the inner periphery 102 of a receptacle body 101 of a receptacle 27 of a light source console. The groove 106 is so positioned as to receive the contacts 26 of the connector 11 when the connector 11 is fully fitted in the receptacle body 101. Thirdly, in the groove 106 there are secured spring contacts 28 each formed by bending a metal strip in the form of letter v. These contacts 28 are so positioned as to come into contact with the corresponding contacts 26 of the connector 11 when the connector 11 is fully fitted in the receptacle body 101. There is provided a ring member 107 with one end screw-engaged with the end of the insulating member 18 and with the other end connected to a flexible sheath 21.

An annular V-groove 29 is formed in the outer periphery of the ring member 107. A clip ball 30 is provided in the inner periphery of the receptacle body 101. The ball 30 is held by a support 31 provided in the inner periphery 102 of the receptacle body 101 and is resiliently urged by a compression spring 32 toward the outer periphery of the ring member 107. When the connector 11 is fully fitted in the receptacle body 101, the ball 30 engages the V-groove 29 of the connector 11, thus ensuring a steadfast engagement of the connector 11 with the receptacle 27. While the connector 11 engages the receptacle 27, the connector 11 can be rotated. Despite such rotation of the connector 11, the ring contacts 26 are kept in contact with the spring contacts 28 of the receptacle 27. Since the connector 11 can freely rotate as a light guide cable 12 is rotates during the endoscope operation, the light guide cable 12 would not be broken by an excess twisting. For the same reason, the connector 11 helps enhance the efficiency of endoscope operation. Alternatively, the ring member 107 may be formed integrally with the connector body 13 or the insulating member 18.

Figure 10:
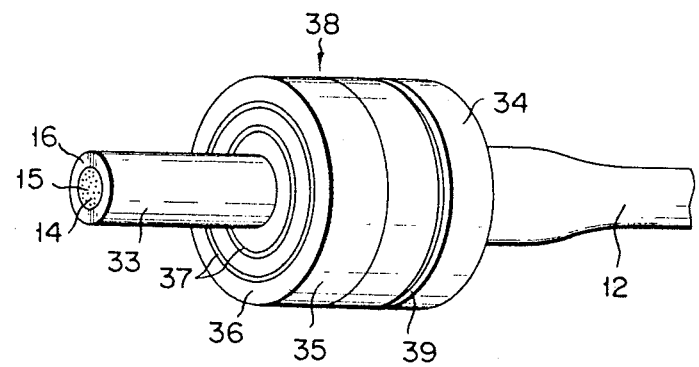
FIGS. 10 to 12 are perspective views of other connectors according to this invention.

FIG. 10 shows another connector 38 according to this invention, which comprises a cylindrical connector body 33, an electrically insulating member 35 and a ring member 34. A light guide 14 extends through the connector body 33. One end of the connector body 33 is formed flush with a light-receiving face 15 of the light guide 14. The insulating member 35 is a hollow cylindrical member surrounding the proximal end portion of the connector body 33 and having an outer diameter larger than that of the connector body 33. The ring member 34 having the same outer diameter as the insulating member 35 is connected to the proximal end of the insulating member 35.

In distal end face 36 of the insulating member 35, ring contacts 37 are embedded concentrically and their outer surfaces are substantially flush with the distal end face 36 of the member 35. An annular V-groove 39 is formed in the outer periphery of the ring member 34.

A receptacle (not shown) for receiving the connector 38 has a hole having a shape complementary to that of the connector 38 and a step portion corresponding to the end face 36 of the insulating member 35. On the step portion of the receptacle there are provided contacts which come into contact with the corresponding ring contacts 37 of the connector 38 when the connector 38 is fully fitted in the hole. Further, a clip ball, a support and a compression spring which are similar to the clip ball 30, support 31 and compression spring 32 shown in FIG. 9 are provided in the inner periphery of the receptacle. The clip ball falls into the V-groove 39 of the connector 38 when the connector 38 is fully fitted in the receptacle, thereby putting the connector 38 in a steadfast engagement with the receptacle. As in the embodiments thus far described, lead wires are connected to the ring contacts 37 of the connector 38 and the contacts of the receptacle. The insulating member 35 and the ring member 43 may be formed integrally.

Figure 11:
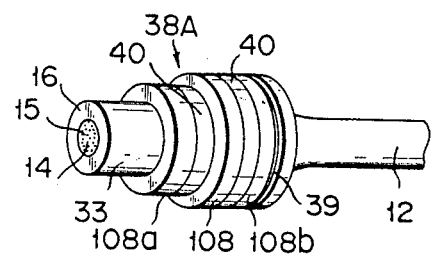

FIG. 11 illustrates another connector 38A which comprises a hollow cylindrical connector body 33 and a hollow cylindrical insulating member 108. A light guide 14 extends through the connector body 33. The light guide 14 has its light-receiving face 15 flush with the distal end face 16 of the connector body 33. The insulating member 108 comprises a small diameter portion 108a and a large diameter portion 108b and thus has a step portion. The insulating member 108 surrounds the proximal end portion of the connector body 33, with the small diameter portion 108a located nearer to the light-receiving face 15 than the large diameter portion 108b. Two ring contacts 40 are embedded in the outer peripheries of the portions 108a and 108b, respectively, with their outer surfaces substantially flush with the outer peripheries of the portions 108a and 108b. An annular V-groove 39 is formed in the outer periphery of the large diameter portion 108b and in a position farther from the light-receiving face 15 than the position where the ring contact 40 is provided.

Figure 12:
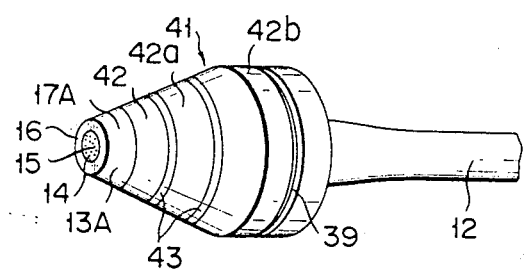

FIG. 12 shows another connector 41 which is shaped like a truncated cone. The connector 41 comprises a hollow cylindrical connector body 13A and an electrically insulating member 42. The connector body 13A comprises a frustoconical head 17A and a cylindrical stem portion (not shown). The stem portion, which is similar to the stem portion 19 shown in FIG. 4, extends through the insulating member 42. The insulating member 42 comprises a truncated conical portion 42a which is continuously connected to the head 17A and a cylindrical skirt portion 42b which is continuously connected to the portion 42a. Two ring contacts 43 are embedded in the outer periphery of the portion 42a with its outer surface substantially flush with the outer periphery of the portions 42a. An annular V-groove 39 is formed in the outer periphery of the skirt portion 42b. A light guide 14 extends through the body 13A. The light guide 14 has its light-receiving face 15 positioned flush with the distal end face 16 of the head 17A of the connector body 13A.

Though not shown, the receptacles for receiving the connector 38A of FIG. 11 and the connector 41 of FIG. 12 have holes the shapes of which are complementary to those of these connectors, respectively. On the inner periphery of the receptacle for the connector 38A there are provided contacts which come into contact with the ring contacts 40 when the connector 38A is fully fitted in the receptacle. Similarly, on the inner periphery of the receptacle for the connector 41 there are provided contacts which come into contact with the ring contacts 43 when the connector 41 is fully set in the receptacle. Further, each of these receptacles is provided with such a clip ball, a support and a compression spring as are shown in FIG. 9 and are described with reference to FIGS. 9 and 10.

Figure 13:
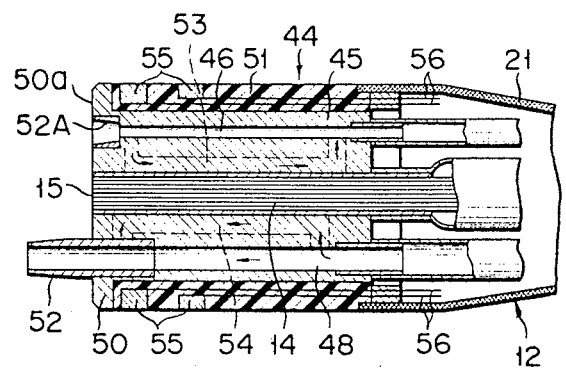
FIG. 13 is a longitudinal cross sectional view of a further embodiment of a connector according to this invention.
Figure 14:
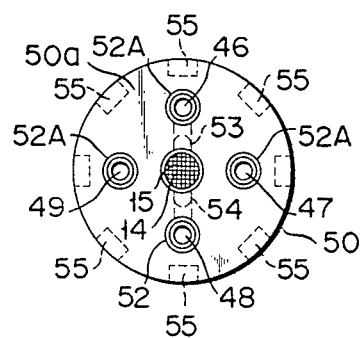
FIG. 14 is a front view of the connector shown in FIG. 13.

FIGS. 13 and 14 illustrate another connector 44 according to this invention. The connector 44 comprises a cylindrical connector body 45 having a flange 50a at one end 50 and a hollow cylindrical electrically insulating member 51 surrounding the connector body 45. A light guide 14 extends through the connector body 45 and has its light-receiving face 15 placed substantially flush with the distal end 50 of the connector body 45.

Through the connector body 45 extend a water supply passage 46, an air supply passage 47 (FIG. 14), a suction passage 48 and a gas passage 49 (FIG. 14)—all extending parallel to the light guide 14. The passages 46, 47 and 49 communicate each at one end respectively with three fittings 52A which are embedded in the end 50 of the connector body 45. Each of these fittings 52A has a truncated conical hole whose inner diameter increases toward the end 50 of the connector body 45 such that the fittings 52A are easily connected to a water supply tube, an air supply tube and a gas supply tube (not shown). The suction passage 48 may communicate with a fitting similar to the fitting 52A or with such a fitting 52 as shown in FIG. 13. The fitting 52 protrudes from the distal end 50 of the connector body 45 with its outer diameter decreasing toward its outer tip. If the fitting 52 is used, a suction tube (not shown) is more easily connected to the suction passage 48 than if the fitting 51 is used. As long as only one protruding fitting is used, it can be easily cleaned and dried. The passages 46, 47, 48 and 49 are connected at the other end to respective tubes which extend through a flexible sheath 21 of a light guide cable and which are connected to corresponding channels (not shown) in an endoscope.

Further, a pair of bypasses 53 and 54 are formed in the connector body 45. The bypasses 53 and 54 extend parallel to, and very close to, the light guide 14 and branch from the water supply passage 46 and the suction passage 48, respectively. A portion of water flowing through the passage 46 and a portion of gas flowing through the passage 48 flow through the bypasses 53 and 54, respectively, to cool the light guide 14 and prevent the connector 44 from becoming too hot.

A plurality of strip contacts 55 are embedded in the outer periphery of the insulating member 51, with their outer surfaces substantially flush with the outer periphery of the member 51. Lead wires 56 extend from the corresponding contacts 55 axially in the insulating member 51 and through the flexible sheath 21 and are connected to an electric circuit provided in the endoscope.

A receptacle into which the connector 44 is fitted has a hole having a shape complementary to that of the connector 44. On the inner periphery of the receptacle these are provided contacts which come into contact with the contacts 55 when the connector 44 is fully fitted in the receptacle.

As in the mebodiments of FIGS. 5 to 7, the insulating member 51 has not in its outer periphery any holes to which the fluid passages 47, 48 and 49 are connected. Thus, its entire outer periphery can be used for embedding only the contacts.

What we claim is:

1. A connector for a light guide cable of an endoscope, comprising a connector body received in that hole of a receptacle which has a complementary shape to the connector body and having two ends, one end being connected to a light guide cable of an endoscope and the other end being flush with a light-receiving face of a light guide which is inserted in the connector body and extends through the light guide cable; an electrically insulating member surrounding the connector body and having an outer periphery; and contacts embedded in the insulating member, having each an outer surface substantially flush with the outer periphery of the insulating member and connected to lead wires which axially extend in the insulating member and through the light guide cable, and wherein at least one fluid passage extending parallel to said light guide is formed in said connector body.

2. The connector according to claim 1, wherein said insulating member has a circular cross section.

3. The connector according to claim 2, wherein said insulating member is a cylindrical member.

4. The connector according to claim 3, wherein said connector body comprises a head having the same outer diameter as an diameter of said insulating member, and a stem portion disposed in said insulating member and having an outer diameter smaller than the outer diameter of said insulating member.

5. The connector according to claim 4, wherein said contacts are strip contacts.

6. The connector according to claim 5, wherein said head has an outer periphery in which a groove is formed to extend axially of the connector so as to set the connector in position.

7. The connector according to claim 4, wherein said contacts are ring contacts.

8. The connector according to claim 2, wherein said connector body is a cylindrical member, and said insulating member is a hollow cylindrical member having an outer diameter larger than the outer diameter of said connector body.

9. The connector according to claim 8, wherein said contacts are embedded in the outer periphery of said insulating member.

10. The connector according to claim 9, wherein said contacts are ring contacts.

11. The connector according to claim 10, wherein an annular groove is formed in the outer periphery of said insulating member so as to set the connector in position.

12. The connector according to claim 8, wherein said contacts are embedded in an end face of said insulating member, which is close to said other end of said connector body.

13. The connector according to claim 12, wherein said contacts are ring contacts.

14. The connector according to claim 13, wherein an annular groove is formed in the outer periphery of said insulating member so as to set the connector in position.

15. The connector according to claim 8, wherein said insulating member comprises a small diameter portion which is close to said other end of said connector body and a large diameter portion which is remote from said other end of said connector body, and said contacts are embedded in the outer periphery of said small diameter portion.

16. The connector according to claim 15, wherein said contacts are ring contacts.

17. The connector according to claim 15, wherein an annular groove is formed in the outer periphery of said large diameter portion so as to set the connector in position.

18. The connector according to claim 2, wherein said insulating member is a truncated conical member and has an outer diameter decreasing toward said other end of said connector body.

19. The connector according to claim 18, wherein said contacts are ring contacts.

20. The connector according to claim 19, wherein an annular groove is formed in the outer periphery of said insulating member so as to set the connector in position.

21. The connector according to claim 1, wherein said insulating member has a non-circular cross section.

22. The connector according to claim 21, wherein said contacts are strip contacts.

23. The connector according to claim 21, wherein said insulating member has a semicircular cross section.

24. The connector according to claim 21, wherein said insulating member has a polygonal cross section.

25. A connector for a light guide cable of an endoscope, comprising a connector body having two ends, one end being connected to a light guide cable of an endoscope and the other end being flush with a light-receiving face of a light guide which is inserted in the connector body and extends through the light guide cable; an electrically insulating member surrounding the connector body and having an outer periphery; contacts embedded in the insulating member, each having an outer surface substantially flush with the outer periphery of the insulating member and connected to lead wires which axially extend in the insulating member and through the light guide cable; at least one fluid passage formed in the connector body and extending parallel to the light guide; and a by-pass passage connected to the fluid passage in the connector body, disposed close to the light guide and extending parallel to the light guide so as to allow passage of a fluid for cooling the light guide.

* * * * *